(12) United States Patent
Gonen et al.

(10) Patent No.: US 12,195,372 B2
(45) Date of Patent: Jan. 14, 2025

(54) PROCESSES FOR REGENERATION OF ORGANOCATIONS

(71) Applicant: TOXSORB LTD., Giladi (IL)

(72) Inventors: Yotam Gonen, Gailadi (IL); Rotem Sade, Giladi (IL); Ohad Shiftan, Giladi (IL); Amos Rauch, Giladi (IL)

(73) Assignee: TOXSORB LTD., Kibbutz Kfar Giladi (IL)

( * ) Notice: Subject to any disclaimer, the term of this patent is extended or adjusted under 35 U.S.C. 154(b) by 1085 days.

(21) Appl. No.: 16/976,216

(22) PCT Filed: Feb. 27, 2019

(86) PCT No.: PCT/IL2019/050223
§ 371 (c)(1),
(2) Date: Aug. 27, 2020

(87) PCT Pub. No.: WO2019/167043
PCT Pub. Date: Sep. 6, 2019

(65) Prior Publication Data
US 2021/0002153 A1 Jan. 7, 2021

(30) Foreign Application Priority Data
Feb. 27, 2018 (IL) ......................................... 257768

(51) Int. Cl.
*C02F 1/52* (2023.01)
*C01B 11/18* (2006.01)
*C02F 1/04* (2023.01)
*C07C 209/86* (2006.01)
*C07C 211/63* (2006.01)

(52) U.S. Cl.
CPC .............. *C02F 1/52* (2013.01); *C01B 11/18* (2013.01); *C02F 1/04* (2013.01); *C07C 209/86* (2013.01); *C07C 211/63* (2013.01); *C02F 2303/18* (2013.01)

(58) Field of Classification Search
CPC combination set(s) only.
See application file for complete search history.

(56) References Cited

U.S. PATENT DOCUMENTS

| | | | |
|---|---|---|---|
| 3,420,621 A * | 1/1969 | Cziesla | C01B 21/1454 423/462 |
| 6,066,257 A | 5/2000 | Venkatesh et al. | |
| 10,112,851 B2 * | 10/2018 | Gonen | C02F 1/5272 |
| 2002/0132866 A1 | 9/2002 | Even et al. | |
| 2010/0176061 A1 | 7/2010 | Monzyk et al. | |

FOREIGN PATENT DOCUMENTS

WO 2014/128702 A1 8/2014

OTHER PUBLICATIONS

KR 2016148971 A (Year: 2016).*
International Search Report for correspondence PCT Application No. PCT/IL2019/050223 mailed May 13, 2019.

* cited by examiner

*Primary Examiner* — Joseph D Anthony
(74) *Attorney, Agent, or Firm* — Wood, Phillips, Katz, Clark & Mortimer

(57) ABSTRACT

The present disclosure concerns processes for regenerating organocations from perchlorate-rich waste products, more specifically transformation of water-insoluble organocation-perchlorate salt, originating from perchlorate-removal water treatment processes, into a water-soluble perchlorate salt for reusing same.

19 Claims, 2 Drawing Sheets

PROCESSES FOR REGENERATION OF ORGANOCATIONS

TECHNOLOGICAL FIELD

The present disclosure concerns processes for regenerating organocations from perchlorate-rich waste products, more specifically transformation of water-insoluble organocation-perchlorate salt, originating from perchlorate-removal water treatment processes, into a water-soluble perchlorate salt for reusing same.

BACKGROUND ART

References considered to be relevant as background to the presently disclosed subject matter are listed below:
WO 2014/128702
Acknowledgement of the above references herein is not to be inferred as meaning that these are in any way relevant to the patentability of the presently disclosed subject matter.

BACKGROUND

Perchlorate is one of the contaminants increasingly found in wastewater, groundwater, surface water and soil. Perchlorate is known for its adverse effects to human health by interfering with iodide uptake into the thyroid gland. It is highly soluble in water and organic solvents, and is difficult to complex with common organic or inorganic cations. Large scale operations for removal of perchlorate from contaminated water, e.g. industrial waste water, require regeneration processes of the perchlorate-removal treatment media, often resulting in the formation of perchlorate-rich brines, which then need to be further processed, rendering the process costly and environmentally problematic.

This is of significant magnitude when highly perchlorate-contaminated water is to be treated, i.e. water containing >10 ppm of perchlorate, where the need to treat the perchlorate-rich brines often renders the removal process economically unfavorable.

Other proposed methods to treat perchlorate-rich waste products from water treatment processes involve bacterial decomposition of perchlorate. However, such processes are relatively slow, suitable for treating relatively low concentrations of perchlorate in the waste product, and require constant monitoring and maintenance of strict conditions throughout the process.

Therefore, there is a need for an efficient and rapid process for the regeneration of a perchlorate-rich waste product into a usable reagent for further use in water-treatment processes, which is also cost effective.

GENERAL DESCRIPTION

Perchlorate is considered to be an anion which does not tend to precipitate from aqueous solutions due to its low charge density, which limits its ability to form ionic bonds with conventional precipitating cations. In WO 2014/128702, the inventors of the present invention have demonstrated a process for precipitation of perchlorate by using benzalkonium (BNZ) as a cation, resulting is precipitation of water-insoluble benzalkonium-perchlorate salt. This process is used to effectively remove high concentrations of perchlorate from perchlorate-contaminated aqueous solutions, e.g. waste water.

The present disclosure aims at providing a process for treating perchlorate-rich waste products that are generated during processes for removal of perchlorate ions from contaminated water. More specifically, the present disclosure concerns processes for treating water insoluble organocation-perchlorate salts, such as those generated in a process described in WO 2014/128702, in order to regenerate the organocation for further use.

The present disclosure is based on the realization that different perchlorate salts have different solubility in various solvents, such that different precipitation reactions can result in recovery of the organocations from the organocation-perchlorate salt.

Thus, in a first aspect, this disclosure provides a process for recovering a water-soluble organocation salt from a substantially water-insoluble organocation-perchlorate, the process comprising:

(a) contacting said substantially water-insoluble organocation-perchlorate with a first solution containing a first salt dissolved in an organic solvent, the first salt consisting of a metal cation and a balancing anion, under conditions permitting precipitation of metal-perchlorate salt and formation of a second salt dissolved in said organic solvent, the second salt consisting of the organocation and the balancing anion;

(b) separating the metal-perchlorate salt from the organic solvent in which the second salt is dissolved; and (c) separating the organic solvent from the second salt to obtain said second salt, said second salt being water-soluble.

In other words, the process is based on the following chemical Equation (I):

(Equation I)

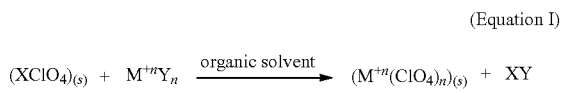

wherein: X is an organocation, M is a metal cation, Y is a balancing anion, and n is an integer between 1 and 3.

As evident from the equation above, the process of this disclosure enables obtaining the organocation in a water-soluble form (e.g. a water-soluble salt) by recovery from a water-insoluble salt of the organocation. This is permitted by taking advantage of the difference in solubility of different salts of the organocation in various organic solvents. The water-insoluble organocation-perchlorate salt ($XClO_4$) is dissolved in organic solvent in which a first salt containing a metal cation and a balancing anion is also dissolved. The dissolution-precipitation reaction results in the formation of a metal-perchlorate salt, which is insoluble in the organic solvent and hence precipitates out of the solvent, and a second salt (XY, containing the organocation and the balancing anion) which is highly soluble in both the organic solvent and water. Thus, the organocation is recovered from its water-insoluble form and transformed into a water-soluble salt, such that it may be re-used in water treatment processes.

In the context of the present disclosure, referring to a compound or component as soluble (or any lingual variation thereof) is meant to denote that the compound or component is dissolvable in a liquid (in water or organic solvent, depending on the context) in a substantive extent.

Similarly, when referring to a compound or a component as insoluble or substantially insoluble (or any lingual variation thereof), it is meant to denote that the compound or component has a negligible solubility in a specific liquid. The solubility (as well as insolubility) is typically provided by a Ks value of the component in a given liquid, which is the equilibrium constant of said component in said liquid.

The higher the Ks value, the higher the solubility of said compound or component in said liquid. All solubility values described herein, unless specifically noted otherwise, are provided at room temperature (20-35° C.) and atmospheric pressure.

In some embodiments, the water-insoluble organocation-perchlorate salt has a water solubility of at most $5 \times 10^{-4}$ M (i.e. Ks≤$2.5 \times 10^{-7}$).

In other embodiments, the water-insoluble organocation-perchlorate salt has a solubility of at least 0.05 M in the organic solvent (i.e. Ks≥0.01). In some embodiments, the water-insoluble organocation-perchlorate salt has a solubility of at least 0.01 M in the organic solvent (i.e. Ks≥0.01).

In some other embodiments, the metal-perchlorate salt has a solubility of at most $10^{-3}$ M in the organic solvent (i.e. Ks≤$10^{-6}$).

In yet other embodiments, the second salt has a water solubility of at least $10^{-4}$ M (i.e. Ks≥$10^{-8}$).

It should be noted, that the term solution should be given its broadest definition to encompass a liquid state in which one component is dissolved in another or in a liquid medium.

Due to its low solubility in the organic solvent, the metal-perchlorate salt is said to precipitate out of the organic solvent. The term precipitating, or any lingual variation thereof, refers to the formation of solid perchlorate salt which is substantially insoluble is the organic solvent and thus sediments (i.e. precipitates) out of the organic solvent as a solid product. By the process of precipitation, the separation of perchlorate from the organocation is obtained.

The term organocation refers to a cation (a positive-charge ion) that has an organic moiety. In some embodiments, the organocation is quaternary ammonium ion. In other embodiments, the organocation is a quaternary ammonium cation having a structure of formula (I):

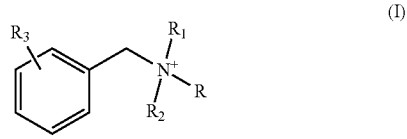

(I)

wherein
R is a —($C_3$-$C_{18}$)alkyl;
$R_1$ and $R_2$ are each independently selected from H and —($C_1$-$C_6$)alkyl; and
$R_3$ is one or more substituents, each independently selected from H, —($C_1$-$C_6$)alkyl, —($C_1$-$C_6$)alkoxy, —NHCO($C_1$-$C_6$)alkyl, —OH, and —$NH_2$.

As used herein, alkyl carbon chains, if not otherwise specified, contain from 1 to 18 carbons, or 1 or 2 or 3 to 18 carbons, and are straight or branched. The term "$C_1$-$C_6$ alkyl" should be understood to encompass any straight or branched alkyl moiety having 1, 2, 3, 4, 5 or 6 carbon atoms. Exemplary alkyl groups include, but are not limited to, methyl, ethyl, propyl, isopropyl, isobutyl, n-butyl, sec-butyl, tert-butyl, and isohexyl.

As used herein, "alkoxy" refers to R'O—, in which R' is a ($C_1$-$C_6$)alkyl.

In reference to group $R_3$, substituent on an aryl moiety, it is said that each represents "one or more substituent", namely one or two or three or four or five substitutions on the ring. When the ring bears one $R_3$ group, this single group may be a substituent positioned on any one of the ring positions, i.e., ortho, meta, or para. When the ring is substituted by two $R_3$ substituting groups, the two groups may be on neighboring carbon atoms (ortho to each other), or may be separated by one or more ring carbon atoms. When the ring is substituted by three or more substituting groups, the groups may be substituted on any one of the ring positions at any variation available.

In some embodiments, $R_1$ and $R_2$ are each independently selected from H and a methyl.

In other embodiments, $R_3$ is one or more substituent, each independently selected from H, methyl, ethyl and propyl.

In additional embodiments, $R_1$ and $R_2$ are both H, and $R_3$ is a methyl.

In some other embodiments, $R_1$, $R_2$ and $R_3$ are H.

According to some embodiments, R is a —($C_6$-$C_{18}$)alkyl. In such embodiments, R may be a —($C_{12}$-$C_{18}$)alkyl.

In additional embodiments, the compound of formula (I) is benzalkonium, wherein R is —($C_3$-$C_{18}$)alkyl. In some additional embodiments, the compound of formula (I) is benzalkonium, in which R is —($C_3$-$C_{18}$)alkyl.

In further embodiments, the compound of formula (I) is a benzalkonium salt, in which R is —($C_{12}$-$C_{18}$)alkyl.

In the process of this disclosure, the organocation-perchlorate is reacted with a first salt that contains a metal cation and a balancing anion. The reaction results in formation of a metal-perchlorate salt or complex and a second salt that contains the organocation and the balancing anion. The metal can be any suitable metal ion, typically an alkali or earth-alkali metal, e.g. sodium, potassium, calcium, magnesium, etc. In some embodiments, the metal is potassium. In other embodiments, the metal is sodium. In further embodiments, the metal is calcium. In yet further embodiments, the metal is magnesium.

The balancing anion can be any suitable balancing anion that forms a first salt with the metal cation that is soluble in the organic solvent and a second salt with the organocation which is soluble in both the organic solvent and water, such as hydroxyl, halide, carboxyl, oxyanion, etc.

In some embodiments, the balancing anion is hydroxyl (OH⁻). In other embodiments, the balancing anion is a halide or a pseudo-halide.

The organic solvent is selected such that it permits high solubility of the organocation-perchlorate, the first salt and the second salt, however in which metal-perchlorate is substantially insoluble. In order to facilitate easy separation of the products of the reaction from the organic solvent, the organic solvent is typically selected to have a low boiling temperature, e.g. below about 90° C.

In some embodiments, the organic solvent may be selected from ethanol, isopropanol, acetone, methanol, and mixtures thereof.

In other embodiments, the solvent is ethanol.

As noted above, it is often desired to separate the reaction products from the organic solvent in order to permit utilization of the reaction products. Thus, in some embodiments, the separating in step (c) may be carried out by evaporation of the organic solvent. In other embodiments, the separating in step (c) may be carried out by distillation.

In such embodiments, the process may further comprise condensing vapors of the organic solvent formed during evaporation or distillation of step (c) to obtain a condensate of organic solvent. The condensate of the organic solvent may then by utilized as a by-product of the process, or, in some embodiments, the condensate may be reintroduced into the process in step (a).

Separating of the precipitated metal-perchlorate at step (b) may be carried out by any suitable process in which solids are separated from liquids, e.g. sedimentation, decantation, filtration, clarification, centrifugation, cyclonic separation, flotation, etc. In some embodiments, the separating in step (b) is carried out by sedimentation, decantation, filtration or a combination thereof.

The metal-perchlorate salt or complex separated in step (b) may, by some embodiments, be further treated to remove the organic solvent from the metal-perchlorate salt.

The organic solvent may be removed from the metal-perchlorate salt by centrifugation or evaporating, and in some embodiments, the organic solvent removed from the metal-perchlorate salt is reintroduced into the process in step (a) (e.g. when removed by evaporation, the organic solvent vapors may be condensed, and the condensate may then be introduced into the process at step (a)).

In processes of the present disclosure, the water-insoluble organocation-perchlorate salt may be introduced into the process at step (a) in solid form (e.g. power, granules, flakes, pellets, etc.). However, as the water-insoluble organocation-perchlorate salt is typically a product of a perchlorate removal water treatment process, such as that described in WO 2014/128702, the water-insoluble organocation-perchlorate salt is typically introduced into step (a) in the form of an aqueous slurry or sometimes as homogenous oily foam. The term aqueous slurry refers to a liquid mixture of particles of the water insoluble organocation-perchlorate salt and an aqueous medium (e.g. water).

In step (a), the water-insoluble organocation-perchlorate salt is contacted with a solution of the first salt in the organic solvent, under conditions permitting the dissolution-precipitation reaction to take place. As used herein, the term contacting, or any lingual variation thereof, refers to the bringing together of the material to be transformed (i.e., the water insoluble organocation-perchlorate salt) and the first salt in such a way to allow intimate contact between them. The contacting may be, for example, by cross-flow of liquids, by mixing, flowing the solution over a substrate of the organocation-perchlorate salt, etc.

In some embodiments, contacting may be carried out by mixing. Mixing may be carried out by a variety of mixing techniques known in the art. Such techniques may include, but are not limited to, static mixing, cross-counter flow, pneumatic and/or electrically operated mixing stirrer/paddle, magnetic stirring, etc.

Mixing may be carried out by using a reaction vessel, a reaction chamber or a reactor, which may be of any size or shape, and constructed of any material suitable to withstand acidic and/or basic pH conditions, heat and pressure. Non-limiting examples are a pipe reactor, tank reactor, fixed bed reactor, a moving bed reactor, a fluidized bed reactor, a circulating fluidized bed reactor, etc.

The liquids used in the processes of the invention may be fed into the reaction vessel via a liquid feeding unit, capable of transferring said liquid to said reaction vessel. The feeding unit is typically connected to the reaction vessel through appropriate tubing system. Said unit may have metering means for measuring exact amount of liquids transferred to the reaction vessel.

The reactor may further comprise a temperature control unit, such as a heating/cooling unit or a heat exchanger, along with means for controlling said unit in response to autothermic or the absence of autothermic conditions within the reaction chamber; internal temperature gauges for monitoring the reaction's temperature; condensation units, scrubbing units and absorption columns, to afford treatment of gaseous reaction products and gaseous contaminants; baffles of various geometries for controlling the flow profile of substance within the reactor; a top plate that is movable with respect to an outer body of the reactor; a base plate that is movable with respect to an outer body of the reactor; reactants inlets at various angles; products outlets at various angles, etc.

In order to facilitate tailoring of the required amount of the first salt to be mixed with the water-insoluble organocation-perchlorate salt, the process may further comprise determining the organocation-perchlorate concentration in feed of the aqueous slurry prior to mixing with the first salt. Additionally, or alternatively, the process may comprise determining the organocation concentration in the solution during or after mixing in order to establish the efficiency of the organocation recovery. The concentration determination, which may also by carried out in-situ during the mixing, may be carried out by any suitable technique known in the art, such as (but not limited to), ion specific electrode, titration, potentiometric titration, gravimetric analysis, chromatography, etc.

In some embodiments, the process further includes adjusting the concentration of the first salt in the first solution according to the concentration of the water-insoluble organocation-perchlorate salt in the feed stream.

The conditions permitting reaction between the water-insoluble organocation-perchlorate salt and the first salt may be selected from at least one of mixing time, mixing speed, temperature, pH, molar ratio between the reaction components, concentrations of the components, etc.

In some embodiments, the contacting may be carried out for a period of time of between of at least 1 minute.

In some embodiments, the contacting may be carried out at a temperature ranging between about −2 and 80° C. In other embodiments, contacting may be carried out at a temperature ranging between about 10 and 50° C.

According to some embodiments, the concentration of the water-insoluble organocation-perchlorate salt in the aqueous slurry that is fed into step (a) is between about 1 and 100%.

According to some other embodiments, the molar ratio between the water-insoluble organocation salt and the first salt is in a range between 1:1 and 1:10.

In another aspect, the present disclosure provides a process for obtaining water-soluble benzalkonium-hydroxide from substantially water-insoluble benzalkonium-perchlorate, the process comprising:

(a) contacting an aqueous slurry of benzalkonium-perchlorate with a first solution containing potassium hydroxide dissolved in an organic solvent, under conditions permitting precipitation of potassium-perchlorate salt and formation of benzalkonium-hydroxide dissolved in said organic solvent;

(b) separating the precipitated potassium-perchlorate from the organic solvent in which the benzalkonium-hydroxide is dissolve; and (c) separating the organic solvent from the benzalkonium-hydroxide to obtain a water-soluble benzalkonium-hydroxide, benzalkonium having the following formula (I):

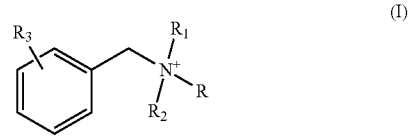

wherein
R is a —($C_3$-$C_{18}$)alkyl;
$R_1$ and $R_2$ are each independently selected from H and —($C_1$-$C_6$)alkyl; and
$R_3$ is one or more substituents, each independently selected from H, —($C_1$-$C_6$)alkyl, —($C_1$-$C_6$)alkoxy, —NHCO($C_1$-$C_6$)alkyl, —OH, and —$NH_2$.

Unlike typical regeneration processes of brines from waste-water treatments, in processes of this disclosure, all of the process products may be used per-se or utilized as starting materials for other processes. For example, the organic solvent, after its separation from the second salt and/or the metal-perchlorate salt, may be used as such in other processes, or may be re-introduced into the process of this disclosure at step (a). In another example, when the metal is potassium, the potassium perchlorate product may be used as an oxidizer to any other desired purpose. When the organocation is benzalkonium, the water-soluble benzalkonium salt may be used in waste-water treatment processes to permit removal of perchlorate ions therefrom (such as those described in WO 2014/128702).

As disclosed herein, the processes of the present disclosure involve numerous process steps which may or may not be associated with other common physical-chemical processes so as to achieve the desired purity and form of each of the isolated components.

As used herein, the singular form "a", "an" and "the" include plural references unless the context clearly dictates otherwise. For example, the term "a compound of formula (I)" may independently include a plurality of compounds of formula (I), including mixtures thereof.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

As used herein, the term "about" is meant to encompass deviation of ±10% from the specifically mentioned value of a parameter, such as temperature, pressure, concentration, etc.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The following description exemplifies how processes of this disclosure may be used to recover a water-soluble form of benzalkonium (BNZ) from water insoluble benzalkonium-perchlorate (BNZ-$ClO_4$) complex. The recovery process is based on the different in solubility of BNZ-$ClO_4$ complex exhibits in water compared to ethanol (Table 1).

TABLE 1

$ClO_4$ equilibrium concentration and solubility in different solvents

| Complex/precipitant | Matrix | $ClO_4$ equilibrium conc. [mM] | Solubility product [Ks] |
|---|---|---|---|
| BNZ-$ClO_4$ | Salt water | 0.81 | $6.56 \times 10^{-7}$ |
| BNZ-$ClO_4$ | Deionized water | 0.20 | $4.04 \times 10^{-8}$ |
| BNZ-$ClO_4$ | Ethanol | 231 | $5.35 \times 10^{-2}$ |
| $KClO_4$ | Ethanol | 0.27 | $7.36 \times 10^{-8}$ |

As clearly evident from Table 1, BNZ-$ClO_4$ solubility product is larger in six orders of magnitude in ethanol compared to the solubility product in deionized water, and five orders of magnitude larger than the solubility in salt water.

Thus, BNZ-$ClO_4$ complex that is a product of water treatment for perchlorate removal by precipitation of BNZ-$ClO_4$ can be treated by dissolving the complex in ethanol, precipitation $ClO_4$ in the ethanol and then evaporating of the ethanol.

Figure 1:
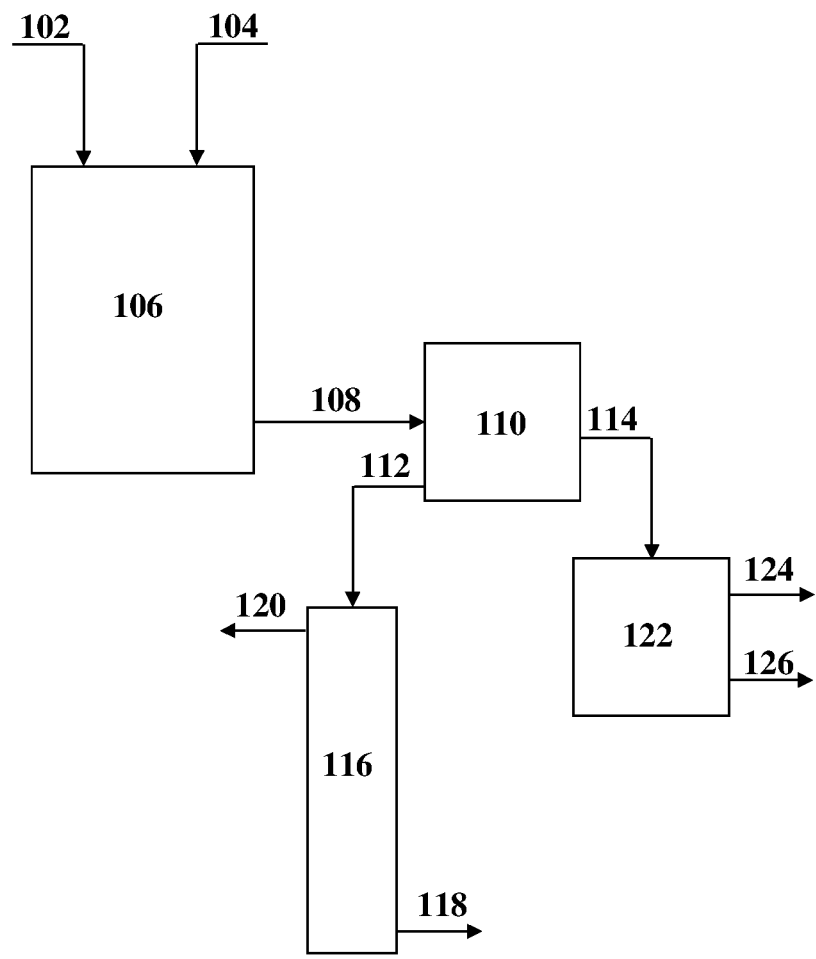
FIG. 1 is a block diagram of a process according to an embodiment of this disclosure.

An exemplary schematic diagram of a process according to this disclosure is shown in FIG. 1. Into reaction vessel 106, a slurry of organocation-perchlorate salt (e.g. BNZ-$ClO_4$) and a solution of a first salt (e.g. KOH dissolved in ethanol) are fed via feeding lines 102 and 104, respectively. The organocation-perchlorate salt and first salt are brought into contact in reaction vessel 106, permitting formation of organic solvent (e.g. ethanol) soluble second salt (e.g. BNZ-OH), and precipitation of metal-perchlorate (e.g. $KClO_4$) in solid form due to its negligible dissolution in ethanol. A stream 108 of second salt dissolved in the organic solvent (e.g. BNZ-OH ethanolic solution) mixed with the solid metal-perchlorate (e.g. $KClO_4$) is fed into a separation unit 110, from which a stream 112 of the solution of the second salt (e.g. BNZ-OH ethanolic solution) is fed into a distillation column 116, separating the solution of the second salt into solvent (e.g. ethanol) 120 and water soluble second salt (which may be in the form of a solid or an aqueous slurry). The second salt (e.g. BNZ-OH) can then be utilized to treat waste water contaminated with perchlorate ions.

From separator 110, a stream 114 of metal-perchlorate in solvent (e.g. $KClO_4$ in ethanol) slurry is transferred into drier 122, in which the solvent and the metal-perchlorate streams (124 and 126, respectively) are separated, to result in metal-perchlorate and solvent products.

Figure 2:
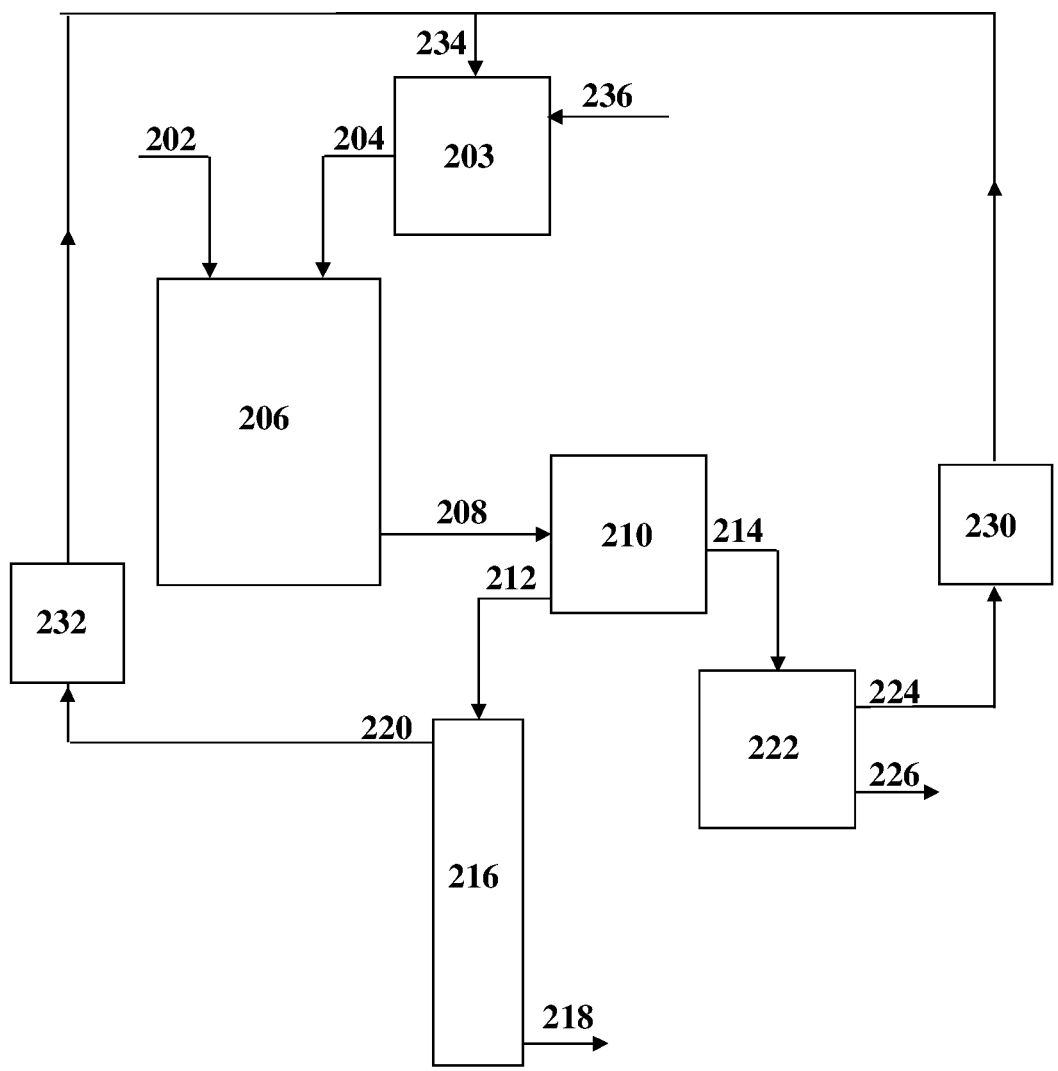
FIG. 2 is a block diagram of process according to another embodiment of this disclosure.

FIG. 2 shows another variation of the process of this disclosure, in which, for the sake of brevity, functionally similar elements to those of FIG. 1 were given like numbers, however shifted by 100. For example, reactor 206 in FIG. 2 has the same functionality as reactor 106 in FIG. 1.

In FIG. 2, the organic solvent vapor stream 220 from the distillation unit 216 is passed through condenser 232 to obtain organic solvent condensate. Similarly, organic solvent vapors stream 224 from drier 222 is passed through condenser 230. The condensate streams are unified into feed line 234, which feeds organic solvent into mixer 203, to which a feed of first salt 236 is also fed. A solution of the first salt in the solvent (e.g. KOH in ethanol) is formed in mixer 203, and then fed as feed stream 204 into reactor 206. In this manner, the organic solvent may be recycled in the process.

An example of a process according to the present disclosure includes first mixing a slurry of water-insoluble organo-cation-perchlorate salt BNZ-$ClO_4$ with an organic solvent, such as ethanol, to dissolve the BNZ-$ClO_4$ in the ethanol. The low solubility of $KClO_4$ in ethanol (i.e. Ks=$7.35 \times 10^{-8}$) allows to separate most of the BNZ from the $ClO_4$ by adding KOH (as the first salt) and precipitating the $ClO_4$ as $KClO_4$ (which is ethanol insoluble). After the precipitation of the $KClO_4$ and separation of the BNZ-OH (being the second salt) solution in ethanol, the ethanol is evaporated and BNZ-OH is recovered, and can be re-used for treating high perchlorate concentration in fresh water brackish water or even brine (e.g. as described in WO 2014/128702).

Results of recovery of BNZ-OH from BNZ-KCLO4 by treating with KOH in ethanol are shown in Tables 2-1 to 2-3.

TABLE 2-1

Step 1: Dissolving BNZ-$ClO_4$ in ethanol

| | | BNZ | | $ClO_4$ | | | |
| | BNZ-$ClO_4$ complex | in complex | in ethanol | in complex | in ethanol | recovery (%) | |
| Test | (g) | (mg) | (mg) | (mg) | (mg) | BNZ | $ClO_4$ |
|---|---|---|---|---|---|---|---|
| 1 | 0.57 | 269.8 | 257.6 | 57.2 | 29.9 | 95.5 | 51.0 |
| 2 | 1.35 | 490.4 | 381.4 | 104.0 | 19.8 | 77.8 | 19.0 |
| 3 | 0.55 | 310.0 | 293.2 | 65.7 | 27.2 | 94.6 | 41.3 |

As seen from Table 2-1, most of the BNZ is dissolved in the ethanol, with most of the tests showing BNZ recovery >90%. This precipitation was clearly evident as white precipitate that settled at the bottom of the tube after few minutes, in contrast to the BNZ-$ClO_4$ complex that floated in the source solution (due to the different densities of these solids—0.94 g/cm$^3$ and 2.2 g/cm$^3$ for BNZ-$ClO_4$ complex and $KClO_4$, respectively).

The recovery of the $ClO_4$ was lower, as once the BNZ-$ClO_4$ complex is dissolved in the ethanol, some $ClO_4$ precipitates as $KClO_4$ in the presence of potassium ions that was attributed to drag out from the source solution (i.e. BNZ-$ClO_4$ slurry) that had K/$ClO_4$ ratio >50.

After dissolving the BNZ-$ClO_4$ in the ethanol, the ethanol contains BNZ, $ClO_4$ and any drag out from the source solution. At this point the goal is to remove as much $ClO_4$ from the ethanol in order to BNZ which is substantially $ClO_4$-free. This is carried out by utilizing potassium ions, in order to precipitate $KClO_4$ out of the ethanol, as shown in Table 2-2.

TABLE 2-2 step 2: Dosing KOH to the ethanol solution

| | | | BNZ (mg) | | $ClO_4$ | | | |
| | | KOH/$ClO_4$ | Before | After | Before | After | | |
| | Ethanol | molar | KOH | KOH | KOH | KOH | Recovery (%) | |
| Test | (ml) | ratio | addition | addition | addition | addition | BNZ | $ClO_4$ |
|---|---|---|---|---|---|---|---|---|
| 1 | 5 | 0.86 | 128.8 | 137.4 | 28.6 | 16.6 | 106.6 | 58.1 |
| 0 | 5 | 2.01 | 190.7 | 182.6 | 9.9 | 8.5 | 95.7 | 85.8 |
| 3 | 8.8 | 1.15 | 252.1 | 250.1 | 23.4 | 3.0 | 99.2 | 12.8 |

As seen from Table 2-2, the addition of KOH reduced the perchlorate concentration from >20 mg/l to <10 mg/l. During this stage no significant loss of BNZ was found as the BNZ recovery was >95%.

The last stage in the BNZ recovery process was evaporation of the ethanol and measurement of the BNZ that was left in the sample. No significant losses of BNZ during evaporation were found, as the recovery of BNZ was ≥95%, as seen from Table 2-3. Recovery that is >100% is attributed to experiment limitation.

TABLE 2-3 step 3: ethanol evaporation

| Test | Ethanol (ml) | BNZ in ethanol (mg) | BNZ recovery after evaporation (mg) | BNZ recovery (%) |
|---|---|---|---|---|
| 1 | 3 | 82.4 | 94.2 | 114.3 |
| 2 | 3 | 109.5 | 114.4 | 104.4 |
| 3 | 0.4 | 11.4 | 10.8 | 95.0 |

The BNZ recovery percentage for each step of the process staged the recovery percentage was >92.9%, and the overall (steps 1+2+3) recovery was 94.4% (±19.9%). This results implies that it is possible to recover the BNZ with efficiency that is close to 100%.

The invention claimed is:

1. A process for recovering a water-soluble organocation salt from a substantially water-insoluble organocation-perchlorate, the process comprising:
   (a) contacting said substantially water-insoluble organo-cation-perchlorate with a first solution containing a first salt dissolved in an organic solvent, the first salt consisting of a metal cation and a balancing anion, under conditions permitting precipitation of metal-perchlorate salt and formation of a second salt dissolved in said organic solvent, the second salt consisting of the organocation and the balancing anion;
   (b) separating the metal-perchlorate salt from the organic solvent in which the second salt is dissolved; and
   (c) separating the organic solvent from the second salt to obtain said second salt, said second salt being a water-soluble organocation salt.

2. The process of claim 1, wherein the separating in step (c) is carried out by evaporation of the organic solvent.

3. The process of claim 2, wherein step (c) further includes condensing vapors of the organic solvent formed during evaporation or distillation to obtain a condensate of organic solvent.

4. The process of claim 1, wherein said separating in step (b) is carried out by sedimentation, decantation, filtration, flotation or a combination thereof.

5. The process of claim 1, wherein metal-perchlorate salt separated in step (b) is further treated to remove the organic solvent from the metal-perchlorate salt.

6. The process of claim 5, wherein the organic solvent is removed from the metal-perchlorate salt by evaporating.

7. The process of claim 6, wherein the organic solvent removed from the metal-perchlorate salt is reintroduced into the process in step (a).

8. The process of claim 1, wherein said substantially water-insoluble organocation-perchlorate salt is introduced into step (a) in the form of an aqueous slurry.

9. The process of claim 1, wherein the molar ratio between the water-insoluble organocation salt and the first salt is in a range between 1:1 and 1:10.

10. The process of claim 1, wherein said organocation is an organocation of formula (I):

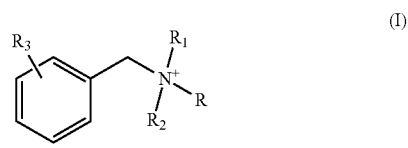

wherein
R is a —($C_3$-$C_{18}$) alkyl;
$R_1$ and $R_2$ are each independently selected from H and —($C_1$-$C_6$) alkyl; and
$R_3$ is one or more substituents, each independently selected from H, —($C_1$-$C_6$) alkyl, —($C_1$-$C_6$) alkoxy, -NHCO ($C_1$-$C_6$) alkyl, —OH, and —$NH_2$.

11. The process of claim 10, wherein $R_1$ and $R_2$ are each independently selected from H and methyl.

12. The process of claim 10, wherein $R_3$ is one or more substituent, each independently selected from H, methyl, ethyl and propyl.

13. The process of claim 10, wherein $R_1$ and $R_2$ are both H, and $R_3$ is a methyl.

14. The process of claim 10, wherein R is a —($C_6$-$C_{18}$) alkyl.

15. The process of claim 1, wherein said metal is selected from sodium, potassium, calcium and magnesium.

16. The process of claim 1, wherein the balancing anion is selected from hydroxyl, carboxyl, halogen, and oxyanion.

17. The process of claim 1, wherein said organic solvent is selected from ethanol, isopropanol, acetone, methanol, and mixtures thereof.

18. A process for obtaining water-soluble benzalkonium-hydroxide from substantially water-insoluble benzalkonium-perchlorate, the process comprising:
   (a) contacting an aqueous slurry of benzalkonium-perchlorate with a first solution containing potassium hydroxide dissolved in an organic solvent, under conditions permitting precipitation of potassium-perchlorate salt and formation of benzalkonium-hydroxide dissolved in said organic solvent;
   (b) separating the precipitated potassium-perchlorate from the organic solvent in which the benzalkonium-hydroxide is dissolve; and
   (c) separating the organic solvent from the benzalkonium-hydroxide to obtain a water-soluble benzalkonium-hydroxide,
   benzalkonium having the following formula (I):

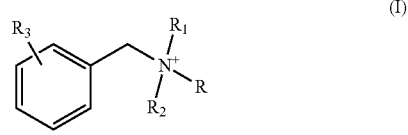

wherein
R is a —($C_3$-$C_{18}$) alkyl;
$R_1$ and $R_2$ are each independently selected from H and —($C_1$-$C_6$) alkyl; and
$R_3$ is one or more substituents, each independently selected from H, —($C_1$-$C_6$) alkyl, —($C_1$-$C_6$) alkoxy, —NHCO($C_1$-$C_6$) alkyl, —OH, and —$NH_2$.

19. The process of claim 18, wherein $R_1$ and $R_2$ are each methyl, $R_3$ is H, and R is a —($C_3$-$C_{18}$) alkyl.

* * * * *